(12) United States Patent
Zhang et al.

(10) Patent No.: US 8,692,036 B2
(45) Date of Patent: Apr. 8, 2014

(54) METHOD FOR PREPARING 2,3-DIMETHYL-2,3-DINITROBUTANE

(75) Inventors: Shengjian Zhang, Ningbo (CN); Yingxian Zhao, Ningbo (CN); Hong Zhang, Ningbo (CN)

(73) Assignee: Ningbo Institute of Technology, Zhejiang University, Zhejiang, Ningbo (CN)

( * ) Notice: Subject to any disclaimer, the term of this patent is extended or adjusted under 35 U.S.C. 154(b) by 0 days.

(21) Appl. No.: 13/823,831

(22) PCT Filed: Sep. 5, 2011

(86) PCT No.: PCT/CN2011/079347
§ 371 (c)(1),
(2), (4) Date: Mar. 15, 2013

(87) PCT Pub. No.: WO2012/159390
PCT Pub. Date: Nov. 29, 2012

(65) Prior Publication Data
US 2013/0184504 A1    Jul. 18, 2013

(30) Foreign Application Priority Data

May 20, 2011    (CN) .......................... 2011 1 0146239
May 20, 2011    (CN) .......................... 2011 1 0146632

(51) Int. Cl.
*C07C 205/00*      (2006.01)

(52) U.S. Cl.
USPC ........................................................ 568/944

(58) Field of Classification Search
USPC ........................................................ 568/944
See application file for complete search history.

(56) References Cited

U.S. PATENT DOCUMENTS 6,911,328 B2      6/2005    Fitzgerald et al.

FOREIGN PATENT DOCUMENTS

CN      1743314      3/2006
RU      2323206      4/2008

OTHER PUBLICATIONS

International Search Report for corresponding International Application No. PCT/CN2011/079347 mailed Mar. 1, 2012 and English translation thereof.

*Primary Examiner* — Jafar Parsa
(74) *Attorney, Agent, or Firm* — Calfee, Halter & Griswold, LLP

(57) ABSTRACT

The present invention relates to a method for preparing 2,3-dimethyl-2,3-dinitrobutane (DMNB), which includes the following steps: (1) making titanium-silicate molecular sieve catalyst, acetone, hydrogen peroxide and ammonia contact and react at 65-80° C. to obtain a modified titanium-silicate molecular sieve catalyst; and (2-1) making acetone oxime and hydrogen peroxide contact and react in the presence of the modified titanium-silicate molecular sieve catalyst and water under the conditions of temperature of 60-90° C. and pH of 8-10, and separating DMNB from the reaction products thereof; or (2-2) making acetone, ammonia and hydrogen peroxide contact and react in the presence of the modified titanium-silicate molecular sieve catalyst and water under the conditions of temperature of 60-90° C. and pH of 8-10, and separating DMNB from the reaction products thereof. By the method provided by the present invention, DMNB can be prepared without having to use dangerous chemicals, such as 2-nitropropane, NaH and the like.

20 Claims, No Drawings

METHOD FOR PREPARING 2,3-DIMETHYL-2,3-DINITROBUTANE

This application is a national phase of International Application No. PCT/CN2011/079347 filed Sep. 5, 2011, which claims priority to Chinese Patent Application No. 201110146632.5, filed May 20, 2011 and Chinese Patent Application No. 201110146239.6, filed May 20, 2011.

FIELD OF THE INVENTION

The present invention relates to a method for preparing 2,3-dimethyl-2,3-dinitrobutane (DMNB).

BACKGROUND OF THE INVENTION

DMNB is an important organic intermediate and has special function and use such as using as a tracer of explosives and the like. The International Civil Aviation Organization (ICAO) issued a document in 1991 to require compulsorily that tracers shall be added in plastic explosives to facilitate the detection of explosives in airports, while DMNB may be used as a tracer in replacement of nitrotoluene. Besides, DMNB is one of the key raw materials for the synthesis of the substances in the category of 2-substitute-1,3-dioxo-4,4,5,5-tetramethylimidazoline. The substances in this category can exclusively capture NO and has important application in medical sector. DMNB is also one of the important raw materials for the synthesis of nitroxide radicals as a main component of molecular magnets. Therefore, it is a matter of significance to researching and developing an efficient, low-consumption, safe and green DMNB synthesis process.

Currently, the methods for synthesis of DMNB mainly include:

Seigle L. W. and Hass H. B. (J. Org. Chem. 1940, 5: 100) reported a method for preparing DMNB through reaction between sodium salt of 2-nitropropane and 2-halogen-2-nitropropane in ethanol solvent. The reaction formula is shown below:

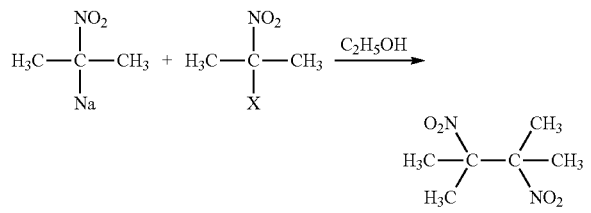

Wherein: X is Cl, Br or I.

The reactant "sodium salt of 2-nitropapane" is prepared through the reaction between metal sodium and anhydrous ethanol at first and then reaction with 2-nitropropane. 2-halogen-2-nitropropane may be obtained through adding halogen into a NaOH solution of 2-nitropropane. When the halogen is Cl, Br and I respectively, the conversion rate of this synthesis reaction is only 9%, 37% and 43%. In this method, highly toxic 2-nitropropane needs to be used.

Tsunoda R. et al (Eur. J. Pharm. 1994, 262: 55) adopted a modified solution: nitropropane is mixed with a NaOH solution at first, then liquid bromine is dropwise added slowly while cooled with ice water, and then ethanol is added to obtain the product through heating and reflux. This method is convenient and its yield is as high as 65~92%, but the quality of the product is poor. As reported in literature, the melting point of the obtained product is 129~130° C. only. Moreover, highly toxic substances such as 2-nitropropane, bromine and the like also need to be used.

Jesse B. M. et al (Org. Lett. 2010, 12: 3522) reported that 2-nitropropane and NaH take reaction at first to generate carbanions, and then CAN (ceric ammonium nitrate) is used to prepare DMNB through oxidation. The yield is 52%. However, this process also needs to use dangerous raw materials such as 2-nitropropane, NaH and the like as well as expensive CAN, so it is not an appropriate synthesis process, either.

To summarize, the currently known methods for synthesis of DMNB all need to use dangerous chemicals, such as: 2-nitropropane, making the production process unsafe, so none of them is suitable for industrial production.

SUMMARY OF THE INVENTION

The object of the present invention is to overcome the shortcoming of the existing methods for synthesis of DMNB: the requirement for the use of dangerous chemicals, and to provide a new method for preparing DMNB.

The present invention provides a method for preparing DMNB comprising the following steps:
(1) making titanium-silicate molecular sieve catalyst, acetone, hydrogen peroxide and ammonia contact and react at 65-80° C. to obtain a modified titanium-silicate molecular sieve catalyst; and
(2-1) making acetone oxime and hydrogen peroxide contact and react in the presence of the modified titanium-silicate molecular sieve catalyst and water under the conditions of temperature of 60-90° C. and pH of 8-10, and separating DMNB from the reaction products thereof; or
(2-2) making acetone, ammonia and hydrogen peroxide contact and react in the presence of the modified titanium-silicate molecular sieve catalyst and water under the conditions of temperature of 60-90° C. and pH of 8-10, and separating DMNB from the reaction products thereof.

By the method for preparing DMNB according to the present invention, DMNB can be prepared without using dangerous chemicals, the production process is safe and industrial production can be easily realized.

Further, the process conditions of the method of the present invention are moderate, the raw materials are readily available and the production cost is low.

DETAILED DESCRIPTION OF THE EMBODIMENTS

According to the first aspect of the present invention, the present invention provides a method for preparing DMNB comprising the following steps:
(1) making titanium-silicate molecular sieve catalyst, acetone, hydrogen peroxide and ammonia contact and react at 65-80° C. to obtain a modified titanium-silicate molecular sieve catalyst; and
(2-1) making acetone oxime and hydrogen peroxide contact and react in the presence of the modified titanium-silicate molecular sieve catalyst and water under the conditions of temperature of 60-90° C. and pH of 8-10, and separating DMNB from the reaction products thereof; or
(2-2) making acetone, ammonia and hydrogen peroxide contact and react in the presence of the modified titanium-silicate molecular sieve catalyst and water under the conditions of temperature of 60-90° C. and pH of 8-10, and separating DMNB from the reaction products thereof.

According to the method of the present invention, in Step (1), the purpose of the contacting and reaction of titanium-silicate molecular sieve catalyst, acetone, hydrogen peroxide and ammonia is to lower the catalytic activity of titanium-silicate molecular sieve catalyst in an oximation reaction system. Further, the inventor of the present invention has unexpectedly discovered that after the catalytic activity of the titanium-silicate molecular sieve catalyst is lowered to a specific level in the oximation reaction system, the obtained modified titanium-silicate molecular sieve catalyst shows high catalytic activity in Step (2). Preferably, the process in Step (1) lowers the catalytic activity of the titanium-silicate molecular sieve catalyst in the oximation reaction to about 60% or less. In other words, in the oximation reaction process such as the process for preparing acetone oxime from acetone under the condition that the molar ratio between acetone and hydrogen peroxide is about 1:1, the conversion rate of acetone is reduced to about 60% or less, preferably 40-50%, by using the modified titanium-silicate molecular sieve catalyst.

Under the preferred condition, in Step (1), titanium-silicate molecular sieve catalyst repeatedly contacts and reacts with acetone, hydrogen peroxide and ammonia for many times, or the continuous material flow of acetone, hydrogen peroxide and ammonia takes long-time contacting and reaction with titanium-silicate molecular sieve catalyst to lower the catalytic activity of titanium-silicate molecular sieve catalyst in the oximation reaction system, thereby raising the catalytic activity of such obtained titanium-silicate molecular sieve catalyst during the process for making acetone oxime and hydrogen peroxide contact and react for preparation of DMNB.

In an embodiment, the performance for making titanium-silicate molecular sieve catalyst repeatedly contacts and reacts with acetone, hydrogen peroxide and ammonia for many times includes: titanium-silicate molecular sieve catalyst, acetone, ammonia and hydrogen peroxide are mixed and contact with each other for 0.1-1 h, the solid precipitate is separated from the resulted mixture, then the solid precipitate, acting as the titanium-silicate molecular sieve catalyst, is mixed and contact with acetone, ammonia and hydrogen peroxide, and the above operation is repeated 6-10 times to reuse the solid precipitate.

According to the method of the present invention, in Step (1), the preferred weight ratio between titanium-silicate molecular sieve catalyst and acetone is 1:5-20 and the more preferred ratio is 1:8-15; the preferred molar ratio among acetone, ammonia and hydrogen peroxide is 1:1-5:0.5-2, and the more preferred ratio is 1:1.5-3.5:0.8-1.5.

According to the method of the present invention, in the case of titanium-silicate molecular sieve catalyst repeatedly contacts and reacts with acetone, hydrogen peroxide and ammonia for many times, when titanium-silicate molecular sieve after contacting and reacting with acetone, ammonia and hydrogen peroxide repeatedly contacts and reacts with acetone, hydrogen peroxide and ammonia, the weight ratio of the titanium-silicate molecular sieve after contacting and reacting with acetone, ammonia and hydrogen peroxide to acetone may be 1:5-20 and the preferred ratio is 1:8-15; the molar ratio among acetone, ammonia and hydrogen peroxide may be 1:1-3:0.5-2, and the preferred ratio is 1:1.5-2.5:0.8-1.5. Further, in each repetition of the contacting and reacting, the conditions and dose of raw materials may be either same or different.

According to the method of the present invention, in Step (1), the titanium-silicate molecular sieve catalyst may be a titanium-silicate molecular sieve catalyst conventionally used in the art. Under the preferred condition, in order to raise the yield of the ultimately prepared DMNB, the preferred titanium-silicate molecular sieve catalyst is a titanium-silicate molecular sieve catalyst with a hollow structure. The radial length of the cavity of the hollow structure of the titanium-silicate molecular sieve is 5-300 nm, and the benzene absorption of the titanium-silicate molecular sieve measured under the condition of 25° C., $P/P_0=0.10$ and 1 h absorption time is at least 70 mg/g, and there is a hysteresis loop between the adsorption isotherm and desorption isotherm of low-temperature nitrogen absorption of the titanium-silicate molecular sieve catalyst. The titanium-silicate molecular sieve catalyst with a hollow structure may be commercially available, for example, it may be the sold TS-1 molecular sieve catalyst. Alternatively, it may also be prepared by a conventional method. Its preparation method may refer to CN1301599A, examples 1-11 thereof in particular.

According to the method of the present invention, in Step (2-1), in the presence of the modified titanium-silicate molecular sieve catalyst ("modified TS catalyst" for short) and water, the reaction between acetone oxime and hydrogen peroxide may be expressed mainly with the following Formula (I).

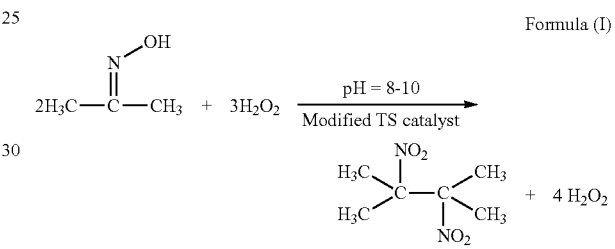

In Step (2-1), the conditions of the contacting and reaction preferably include: pH of 9-10, reaction temperature of 80-90° C., and reaction time of 0.5-2 h.

In Step (2-1), the weight ratio between the modified TS catalyst and acetone oxime may be 5-30:100, preferably 10-15:100; the weight ratio between water and acetone oxime may be 1-10:1, preferably 2-4:1; the molar ratio between acetone oxime and hydrogen peroxide may be 1:1-3, preferably 1:2-2.5.

The water in Step (2-1) may be introduced along with the addition of the hydrogen peroxide solution. Alternatively, partial water may be added separately and the rest water is introduced along with the addition of the hydrogen peroxide solution.

In Step (2-1), the pH value of the reaction system may be adjusted through addition of alkali solution. The alkali solution may be a water solution of any alkali conventionally used in the art. For example, it may be a NaOH solution or ammonia water.

In Step (2-2), in the presence of the modified TS catalyst and water, the reaction among acetone, ammonia and hydrogen peroxide may be expressed mainly with the following Formula (II).

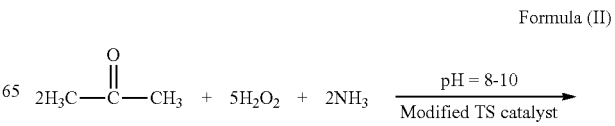

-continued

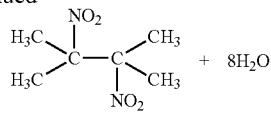 + 8H₂O

In Step (2-2), the conditions of the contacting and reaction preferably include: pH of 9-10, reaction temperature of 80-90° C., and reaction time of 0.5-2 h.

In Step (2-2), the weight ratio between the modified TS catalyst and acetone may be 5-30:100, preferably 10-15:100; the weight ratio between water and acetone may be 1-5:1, preferably 2-4:1; the molar ratio between acetone and hydrogen peroxide may be 1:3-8, preferably 1:4-6.

The water in Step (2-2) may be introduced along with the addition of the hydrogen peroxide solution and ammonia water. Alternatively, partial water may be added separately and the rest water is introduced along with the addition of the hydrogen peroxide solution and ammonia water.

In Step (2-2), the amount of ammonia added in form of ammonia water is mainly used to adjust the pH value of the reaction system to 8-10, preferably 9-10.

According to the method of the present invention, the ammonia in Step (1) and Step (2-2) typically is added in form of ammonia water. The concentration of the ammonia water may be 20-50 wt %.

According to the method of the present invention, the hydrogen peroxide in Step (1), Step (2-1) and Step (2-2) typically is added in form of hydrogen peroxide solution. The concentration of the hydrogen peroxide solution may be 28-50 wt %, preferably 28-30 wt %.

According to the method of the present invention, in Step (1), the reaction among titanium-silicate molecular sieve catalyst ("TS catalyst" for short), acetone, hydrogen peroxide and ammonia pertains to conventional oximation reaction. Its reaction principle may be expressed with the following Formula (III).

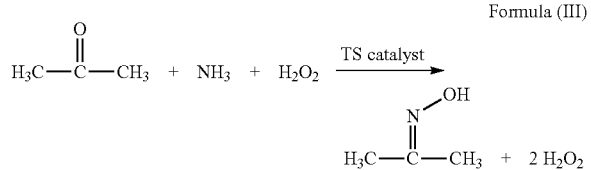

Formula (III)

Obviously, acetone oxime may be generated in Step (1). The raw materials are same as those in Step (2-1).

Therefore, in a preferred embodiment, the method further comprises: separating acetone oxime from the reaction products in Step (1), and reusing the separated acetone oxime as at least part of the acetone oxime raw material in Step (2-1).

In the present invention, the performance for separating the reaction products in Step (1) may include: the reaction products are subjected to solid-liquid separation (such as: centrifugal separation and filtration), the separated solid precipitate repeatedly contacts and reacts with acetone, ammonia and hydrogen peroxide, or the separated solid precipitate is directly used as the modified TS catalyst in Step (2-1) and/or Step (2-2), and the separated liquid is injected into a rectification tower (the theoretic plate number may be 20-80, preferably 30-60), and acetone oxime is collected from bottom liquid through controlling bottom temperature (preferably 80-130° C., more preferably 100-120° C.) and reflux ratio (preferably not less than 2:1, more preferably 5-10:1).

Specifically, the method for collecting acetone oxime from bottom liquid may include: halohydrocarbon is used to extract the bottom liquid 3-5 times, the solution in the extraction layer is collected, the solution in the extraction layer is distilled under normal or reduced pressure at a temperature of 70° C. or less (preferably room temperature to 70° C.), and the solvent is distilled to dryness to obtain acetone oxime.

According to the method of the present invention, in Step (2-1) and Step (2-2), the method for separating DMNB from the reaction products may include: the reaction products are cooled to 0-40° C. and then subjected to solid-liquid separation (such as: centrifugal separation and filtration), acetone is used to wash the solid (mainly including the modified titanium-silicate molecular sieve catalyst) obtained during the solid-liquid separation, the obtained washing solution is mixed with the liquid obtained during the solid-liquid separation, then the obtained mixed solution is evaporated (for example by rotary evaporation) to remove acetone, then it is cooled and filtered, and the solid obtained from the cooling and filtration is washed with water and dried. There are no particular limitations to the conditions of the evaporation, as long as the acetone in the mixed solution can be basically removed.

According to the method of the present invention, some of the acetone oxime added as a reaction raw material in Step (2-1) may be left, and in Step (2-2), with the existence of the modified titanium-silicate molecular sieve catalyst, some acetone may take oximation reaction with hydrogen peroxide and ammonia to generate acetone oxime. Therefore, the reaction products in Step (2-1) and Step (2-2) both contain acetone oxime.

In a preferred embodiment, the method further comprises: in the foregoing process of separating DMNB from the reaction products of Step (2-1) and/or Step (2-2), separating acetone oxime from the liquid obtained from the cooling and filtration process (for example, a extraction separation process with halohydrocarbon as the extracting agent may be used), and reusing the separated acetone oxime as at least part of the acetone oxime raw material in Step (2-1).

Below the present invention is further described in connection with embodiments.

In the following examples and comparison example 1, the conversion rate of acetone and the molar yield of DMNB are calculated with the following calculation formulae.

Conversion rate of acetone=Consumption of acetone/ charge amount of acetone×100%

Molar yield of DMNB=Moles of DMNB product×2/ moles of acetone or acetone oxime added as a reaction raw material in Step (2)×100%

EXAMPLE 1

This example is intended to describe the method for preparing DMNB in the present invention.

(1) Modified Titanium-Silicate Molecular Sieve Catalyst

1 L of water, 1160 g (20 mol) of acetone and 100 g of TS-1 (prepared by the method of example 1 of the patent application CN1301599A) are added in a reactor, then 30 wt % ammonia water containing 36 mol of NH₃ and 30 wt % hydrogen peroxide solution containing 20 mol of H₂O₂ are dropwise added at 70° C., they react 0.5 h at constant temperature after the dropwise addition, and then the solid precipitate is centrifugally separated.

The obtained solid precipitate replaces the foregoing TS-1 to repeat the foregoing process eight times. In the eighth repeated reaction process, the conversion rate of acetone is about 45%. In this way, modified TS-1 catalyst C1 is obtained.

(2) Preparation of DMNB 58 g of water, 29 g (0.50 mol) of acetone and 2.9 g of the foregoing modified TS-1 catalyst C1 are added into a 500 mL three-neck flask installed with a thermometer, a constant-pressure funnel, a reflux cooling device and an electric stirrer, and mixed 0.5 h under electric stirring. Then the solution is heated to 85° C. in a water bath. 30 wt % hydrogen peroxide solution containing 226.6 g (2 mol) of $H_2O_2$ and 30 wt % ammonia water containing 85 g (1.5 mol) of $NH_3$ are dropwise added at the same temperature to adjust the pH value of the mixed material in the flask to 10. They react 0.5 h at constant temperature 90° C. after the dropwise addition, then are cooled to room temperature and then centrifugally separated at 3000 rpm. The separated solid (mainly including modified TS-1 catalyst) is washed with 6 g of acetone twice. The obtained washing solution is mixed with the liquid obtained from centrifugal separation, and rotationally evaporated at 80° C. 0.05 MPa to remove acetone. The remaining liquid is cooled to room temperature and filtered. The solid obtained from the filtration is washed with water and then dried at 70° C. to obtain 19.2 g of (about 0.11 mol) of DMNB product. The molar yield of DMNB is 43.6%. Its melting point is 210.2-212.0° C. Its NMR (nuclear magnetic resonance) data are as follows:

$^1$H NMR (400 Hz, DMSO-d6), δ: 1.71 (s, 2H).
$^{13}$C NMR (100 MHz, DMSO-d6), δ: 23.02, 91.47.

COMPARISON EXAMPLE 1

DMNB is prepared by the method of example 1. The difference is that in Step (2), TS-1 (prepared by the method of example 1 of the patent application CN1301599A) is used to replace the modified TS-1 catalyst C1.

The result indicates no DMNB is detected in the products, in other words no DMNB is generated in this preparation process.

EXAMPLE 2

This example is intended to describe the method for preparing DMNB in the present invention.

DMNB is prepared by the method of example 1. The difference is that in Step (2), the amount of the added water is 116 g. The result indicates the molar yield of DMNB is 45.3%. The melting point of the obtained DMNB product is 210.5-212.1° C.

EXAMPLE 3

This example is intended to describe the method for preparing DMNB in the present invention.

DMNB is prepared by the method of example 1. The difference is that in Step (2), the dose of the modified TS-1 catalyst C1 is 4.3 g. The result indicates the molar yield of DMNB is 45.6%, and the melting point of the obtained DMNB product is 210.2-212.0° C.

EXAMPLE 4

This example is intended to describe the method for preparing DMNB in the present invention.

DMNB is prepared by the method of example 1. The difference is that in Step (2), the temperature for dropwise addition of the hydrogen peroxide solution and the ammonia water is 70° C., and the constant-temperature reaction is taken at 75° C. The result indicates the molar yield of DMNB is 36.5%, and the melting point of the obtained DMNB product is 210.2-212.2° C.

EXAMPLE 5

This example is intended to describe the method for preparing DMNB in the present invention.

DMNB is prepared by the method of example 1. The difference is that in Step (2), the amount of the added hydrogen peroxide solution is 339.3 g, containing about 3 mol of $H_2O_2$. The result indicates the molar yield of DMNB is 53.4%, and the melting point of the obtained DMNB product is 210.1-212.2° C.

EXAMPLE 6

This example is intended to describe the method for preparing DMNB in the present invention.

DMNB is prepared by the method of example 1. The difference is that in Step (1), the obtained solid precipitate replaces the foregoing TS-1 to repeat the foregoing process twice, and the conversion rate of acetone in the second repetition of the reaction process is about 90%, thus obtaining the modified TS-1 catalyst C2; and in Step (2), the modified TS-1 catalyst C2 replaces the modified TS-1 catalyst C1. The result indicates the molar yield of DMNB is 1.6%, and the melting point of the obtained DMNB product is 210.2-212.2° C.

EXAMPLE 7

This example is intended to describe the method for preparing DMNB in the present invention.

(1) Modified Titanium-Silicate Molecular Sieve Catalyst

1 L of water, 500 g (8.6 mol) of acetone and 100 g of TS-1 (prepared by the method of example 2 of the patent application CN1301599A) are added in a reactor, then 30 wt % ammonia water containing 26 mol of $NH_3$ and 30 wt % hydrogen peroxide solution containing 8.6 mol of $H_2O_2$ are dropwise added at 65° C., they react 1 h at constant temperature after the dropwise addition, and then the solid precipitate is centrifugally separated.

The obtained solid precipitate replaces the foregoing TS-1 to repeat the foregoing process six times. In the sixth repeated reaction process, the conversion rate of acetone is about 50%. In this way, modified TS-1 catalyst C3 is obtained.

(2) Preparation of DMNB 116 g of water, 29 g (0.50 mol) of acetone and 3.5 g of the foregoing modified TS-1 catalyst C3 are added into a 500 mL three-neck flask installed with a thermometer, a constant-pressure funnel, a reflux cooling device and an electric stirrer and mixed 1 h under electric stirring. Then the solution is heated to 80° C. in a water bath. 30 wt % hydrogen peroxide solution containing 226.6 g (2 mol) of $H_2O_2$ and 30 wt % ammonia water containing 85 g (1.5 mol) of $NH_3$ are dropwise added at the same temperature to adjust the pH value of the mixed material in the flask to 9. They react 2 h at constant temperature at 80° C. after the dropwise addition, then are cooled to room temperature and then centrifugally separated at 3000 rpm. The separated solid (mainly including modified TS-1 catalyst) is washed with 6 g of acetone twice. The obtained washing solution is mixed with the liquid obtained from centrifugal separation, and rotationally evaporated at 80° C. 0.05 MPa to remove acetone. The remaining liquid is cooled to room temperature and filtered. The solid obtained from the filtration is washed with water and then dried at 70°

C. to obtain 20.9 g (about 0.12 mol) of DMNB product. The molar yield of DMNB is 46.7%. Its melting point is 210.3~212.1° C.

EXAMPLE 8

This example is intended to describe the method for preparing DMNB in the present invention.

(1) Modified Titanium-Silicate Molecular Sieve Catalyst

1 L of water, 2000 g (34.4 mol) of acetone and 100 g of TS-1 (prepared by the method of example 3 of the patent application CN1301599A) are added in a reactor, then 30 wt % ammonia water containing 86 mol of $NH_3$ and 30 wt % hydrogen peroxide solution containing 34.4 mol of $H_2O_2$ are dropwise added at 80° C., they react 0.1 h at constant temperature after the dropwise addition, and then the solid precipitate is centrifugally separated.

The obtained solid precipitate replaces the foregoing TS-1 to repeat the foregoing process ten times. In the tenth repeated reaction process, the conversion rate of acetone is about 40%. In this way, modified TS-1 catalyst C4 is obtained.

(2) Preparation of DMNB 116 g of water, 29 g (0.50 mol) of acetone and 3.5 g of the foregoing modified TS-1 catalyst C4 are added into a 500 mL three-neck flask installed with a thermometer, a constant-pressure funnel, a reflux cooling device and an electric stirrer and mixed 1 h under electric stirring. Then the solution is heated to 80° C. in a water bath. 30 wt % hydrogen peroxide solution containing 226.6 g (2 mol) of $H_2O_2$ and 30 wt % ammonia water containing 85 g (1.5 mol) of $NH_3$ are dropwise added at the same temperature to adjust the pH value of the mixed material in the flask to 8. They react 1 h at constant temperature 85° C. after the dropwise addition, then are cooled to room temperature and then centrifugally separated at 3000 rpm. The separated solid (mainly including modified TS-1 catalyst) is washed with 6 g of acetone twice. The obtained washing solution is mixed with the liquid obtained from centrifugal separation, and rotationally evaporated at 80° C. 0.05 MPa to remove acetone. The remaining liquid is cooled to room temperature and filtered. The solid obtained from the filtration is washed with water and then dried at 70° C. to obtain 21.1 g (about 0.12 mol) of DMNB product. The molar yield of DMNB is 48.3%. Its melting point is 210.2~212.0° C.

EXAMPLE 9

This example is intended to describe the method for preparing DMNB in the present invention.

(1) Modified Titanium-Silicate Molecular Sieve Catalyst 1L of water, 1160 g (20 mol) of acetone and 100 g of TS-1 (prepared by the method of example 1 of the patent application CN1301599A) are added in the reactor, then 30 wt % ammonia water containing 36 mol of $NH_3$ and 30 wt % hydrogen peroxide solution containing 20 mol of $H_2O_2$ are dropwise added at 70° C., they react 0.5 h at constant temperature after the dropwise addition, and then the solid precipitate is centrifugally separated.

The obtained solid precipitate replaces the foregoing TS-1 to repeat the foregoing process eight times. In the eighth repeated reaction process, the conversion rate of acetone is about 45%. In this way, modified TS-1 catalyst C5 is obtained.

The liquids obtained after every centrifugal separation are mixed. The mixed liquid is added to a rectification tower for rectification separation. The theoretical plate number of the rectification tower is 30. The packing is stainless steel wire gauzes. The diameter of the tower is 600 mm and its height is 12 m. The bottom temperature is controlled at 110° C. and the reflux ratio is controlled at 8:1. Then the bottom liquid is cooled to room temperature and extracted with perchloroethylene (PCE) three times. The liquid in the extraction layer is merged and distilled at about 65° C. under reduced pressure. After PCE is evaporated to dryness, acetone oxime product is obtained. Its melting point is 58.2-60.1° C. The data of its infrared spectrum (IR) and mass spectrum (MS) are as follows:

IR, $v_{max}/cm^{-1}$: 3200, 2920, 2896, 1681, 1498, 1371, 1268, 1072, 949, 81;

MS m/z (%): 73 ($M^+$, 100), 58(64), 54(21), 42(21), 41(21), 31(31), 28(42), 15 (45).

(2) Preparation of DMNB 73 g of water, 29.2 g (0.40 mol) of the acetone oxime obtained in the foregoing Step (1) and 2.9 g of the foregoing modified TS-1 catalyst C5 are added into a 500 mL three-neck flask installed with a thermometer, a constant-pressure funnel, a reflux cooling device and an electric stirrer and mixed 0.5 h under electric stirring. Then the solution is heated to 85° C. in a water bath. 30 wt % hydrogen peroxide solution containing 113.3 g (1 mol) of $H_2O_2$ is dropwise added at this temperature and 30 wt % NaOH solution is added to adjust the pH value of the mixed material in the flask to 10. They react 0.5 h at constant temperature 90° C. after the dropwise addition, then are cooled to room temperature and then centrifugally separated at 3000 rpm. The separated solid (mainly including modified TS-1 catalyst) is washed with 6 g of acetone twice. The obtained washing solution is mixed with the liquid obtained from centrifugal separation, and rotationally evaporated at 80° C. 0.05 MPa to remove acetone. The remaining liquid is cooled to room temperature and filtered. The solid obtained from the filtration is washed with water and then dried at 70° C. to obtain 3.9 g (about 0.022 mol) of DMNB product. The molar yield of DMNB is 11.2%. Its melting point is 210.2-212.0° C. Its NMR data are as follows:

$^1$H NMR (400 Hz, DMSO-d6), δ: 1.71 (s, 2H).

$^{13}$C NMR (100 MHz, DMSO-d6), δ: 23.02, 91.47.

COMPARISON EXAMPLE 2

DMNB is prepared as the method of example 9. The difference is that in Step (2), TS-1 (prepared by the method of example 1 of the patent application CN1301599A) is used to replace the modified TS-1 catalyst C5.

The result indicates no DMNB is detected in the products, in other words no DMNB is generated in this preparation process.

EXAMPLE 10

This example is intended to describe the method for preparing DMNB in the present invention.

DMNB is prepared by the method of example 9. The difference is that in Step (2), the amount of the added water is 146 g. The result indicates the molar yield of DMNB is 12.5%, and the melting point of the obtained DMNB product is 210.5-212.1° C.

EXAMPLE 11

This example is intended to describe the method for preparing DMNB in the present invention.

DMNB is prepared by the method of example 9. The difference is that in Step (2), the dose of the modified TS-1 catalyst C1 is 4.3 g. The result indicates the molar yield of DMNB is 11.4%, and the melting point of the obtained DMNB product is 210.2-212.0° C.

EXAMPLE 12

This example is intended to describe the method for preparing DMNB in the present invention.

DMNB is prepared by the method of example 9. The difference is that in Step (2), 30 wt % ammonia water replaces 30 wt % NaOH solution to adjust pH value. The result indicates the molar yield of DMNB is 5.7%, and the melting point of the obtained DMNB product is 210.3-212.2° C.

EXAMPLE 13

This example is intended to describe the method for preparing DMNB in the present invention.

DMNB is prepared by the method of example 9. The difference is that in Step (2), the temperature for dropwise addition of the hydrogen peroxide solution and the ammonia water is 70° C., and the constant-temperature reaction is taken at 75° C. The result indicates the molar yield of DMNB is 8.9%, and the melting point of the obtained DMNB product is 210.2-212.2° C.

EXAMPLE 14

This example is intended to describe the method for preparing DMNB in the present invention.

DMNB is prepared by the method of example 9. The difference is that in Step (2), the amount of the added hydrogen peroxide solution is 90.6 g, containing about 0.8 mol of $H_2O_2$. The result indicates the molar yield of DMNB is 8.6%, and the melting point of the obtained DMNB product is 210.1-212.2° C.

EXAMPLE 15

This example is intended to describe the method for preparing DMNB in the present invention.

DMNB is prepared by the method of example 9. The difference is that in Step (1), the obtained solid precipitate replaces the foregoing TS-1 to repeat the foregoing process twice, and the conversion rate of acetone in the second repetition of the reaction process is about 90%, thus obtaining the modified TS-1 catalyst C6; and in Step (2), the modified TS-1 catalyst C6 replaces the modified TS-1 catalyst C5. The result indicates the molar yield of DMNB is 1.3%, and the melting point of the obtained DMNB product is 210.2-212.2° C.

EXAMPLE 16

This example is intended to describe the method for preparing DMNB in the present invention.

(1) Modified Titanium-Silicate Molecular Sieve Catalyst

The modified TS-1 catalyst C3 is prepared by the method of example 7.

(2) Preparation of DMNB 116 g of water, 29.2 g (0.40 mol) of acetone oxime and 3.5 g of the foregoing modified TS-1 catalyst C3 are added into a 500 mL three-neck flask installed with a thermometer, a constant-pressure funnel, a reflux cooling device and an electric stirrer and mixed 1 h under electric stirring. Then the solution is heated to 80° C. in a water bath. 30 wt % hydrogen peroxide solution containing 113.3 g (1 mol) of $H_2O_2$ is dropwise added at this temperature and 30 wt % NaOH solution is added to adjust the pH value of the mixed material in the flask to 9. They react 2 h at constant temperature 80° C. after the dropwise addition, then are cooled to room temperature and then centrifugally separated at 3000 rpm. The separated solid (mainly including modified TS-1 catalyst) is washed with 6 g of acetone twice. The obtained washing solution is mixed with the liquid obtained from centrifugal separation, and rotationally evaporated at 80° C. 0.05 MPa to remove acetone. The remaining liquid is cooled to room temperature and filtered. The solid obtained from the filtration is washed with water and then dried at 70° C. to obtain 5.0 g (about 0.028 mol) of DMNB product. The molar yield of DMNB is 14.0%. Its melting point is 210.3~212.1° C.

EXAMPLE 17

This example is intended to describe the method for preparing DMNB in the present invention.

(1) Modified Titanium-Silicate Molecular Sieve Catalyst

The modified TS-1 catalyst C4 is prepared by the method of example 8.

(2) Preparation of DMNB 116 g of water, 29.2 g (0.40 mol) of acetone oxime and 3.5 g of the foregoing modified TS-1 catalyst C4 are added into a 500 mL three-neck flask installed with a thermometer, a constant-pressure funnel, a reflux cooling device and an electric stirrer and mixed 1 h under electric stirring. Then the solution is heated to 80° C. in a water bath. 30 wt % hydrogen peroxide solution containing 113.3 g (1 mol) of $H_2O_2$ is dropwise added at this temperature and 30 wt % NaOH solution is added to adjust the pH value of the mixed material in the flask to 8. They react 1 h at constant temperature 85° C. after the dropwise addition, then are cooled to room temperature and then centrifugally separated at 3000 rpm. The separated solid (mainly including modified TS-1 catalyst) is washed with 6 g of acetone twice. The obtained washing solution is mixed with the liquid obtained from centrifugal separation, and rotationally evaporated at 80° C. 0.05 MPa to remove acetone. The remaining liquid is cooled to room temperature and filtered. The solid obtained from the filtration is washed with water and then dried at 70° C. to obtain 4.0 g (about 0.023 mol) of DMNB product. The molar yield of DMNB is 11.3%. Its melting point is 210.2~212.0° C.

As can be seen from the data of the foregoing examples and comparison examples, DMNB can be prepared by the method of the present invention without having to use dangerous chemicals, such as 2-nitropropane, NaH and the like.

What is claimed is:

1. A method for preparing 2,3-dimethyl-2,3-dinitrobutane (DMNB) comprising the following steps:
   (a) reacting a titanium-silicate molecular sieve catalyst with acetone, hydrogen peroxide and ammonia at a temperature from about 65° C. to about 80° C. to obtain a modified titanium-silicate molecular sieve catalyst; and
   (b1) reacting acetone oxime and hydrogen peroxide in the presence of the modified titanium-silicate molecular sieve catalyst and water to obtain a reaction product including 2,3-dimethyl-2,3-dinitrobutane (DMNB), wherein said reaction is performed at a temperature from about 60° C. to about 90° C. and at a pH of about 8 to about 10; or
   (b2) reacting acetone, ammonia and hydrogen peroxide in the presence of the modified titanium-silicate molecular sieve catalyst and water to obtain a reaction product including 2,3-dimethyl-2,3-dinitrobutane (DMNB), wherein said reaction is performed at a temperature of from about 60° C. to about 90° C. and at a pH of about 8 to about 10; and (c) separating the DMNB from the reaction product of (b1) or (b2).

2. The method of claim 1, wherein step (a) further comprises:
   i) reacting the titanium-silicate molecular sieve catalyst, acetone, ammonia and hydrogen peroxide for a period of about 0.1 hours to about 1 hour to obtain a reaction product;
   ii) separating a solid precipitate from the reaction product;
   iii) reacting the solid precipitate with the acetone, ammonia and hydrogen peroxide of step (i), wherein the solid precipitate acts as the titanium-silicate molecular sieve catalyst; and
   iv) repeating steps (i) through (iii) 6-10 times to reuse the solid precipitate.

3. The method of claim 1, wherein the weight ratio between the titanium-silicate molecular sieve catalyst and the acetone of step (a) is 1:5-20, and the molar ratio among acetone, ammonia and hydrogen peroxide is 1:1-3:0.5-2.

4. The method of claim 1, wherein the titanium-silicate molecular sieve catalyst of step (a) is a titanium-silicate molecular sieve catalyst with a hollow structure.

5. The method of claim 1, wherein step (b1) is performed at a pH from about 9 to about 10 and at a temperature from about 80° C. to about 90° C. for about 0.5 hours to about 2 hours.

6. The method of claim 1, wherein the weight ratio between the modified titanium-silicate molecular sieve catalyst and acetone oxime of step (b1) is 5-30:100, the weight ratio between water and acetone oxime is 1-10:1, and the molar ratio between acetone oxime and hydrogen peroxide is 1:1-3.

7. The method of claim 6, wherein the weight ratio between the modified titanium-silicate molecular sieve catalyst and acetone oxime of step (b1) is 10-15:100, the weight ratio between water and acetone oxime is 2-4:1, and the molar ratio between acetone oxime and hydrogen peroxide is 1:2-2.5.

8. The method of claim 1, wherein step (b2) is performed at a pH from about 9 to about 10 and at a temperature from about 80° C. to about 90° C. for about 0.5 hours to about 2 hours.

9. The method of claim 1, wherein the weight ratio between the modified titanium-silicate molecular sieve catalyst and acetone of step (b2) is 5-30:100, the weight ratio between water and acetone is 1-5:1, and the molar ratio between acetone and hydrogen peroxide is 1:3-8.

10. The method of claim 9, wherein the weight ratio between the modified titanium-silicate molecular sieve catalyst and acetone of step (b2) is 10-15:100, the weight ratio between water and acetone is 2-4:1, and the molar ratio between acetone and hydrogen peroxide is 1:4-6.

11. The method of claim 1, wherein further comprising: separating acetone oxime from the reaction products of step (a), and reusing said separated acetone oxime as at least part of the acetone oxime raw material in Step (b1).

12. The method of claim 1, wherein step (c) further comprises:
   i) cooling the reaction products of (b1) or (b2) to a temperature from about 0° C. to about 40° C.;
   ii) separating a solid phase of the reaction product from a liquid phase of the reaction product;
   iii) washing the solid phase of the reaction product with acetone;
   iv) mixing the solution of step (iii) with the liquid phase of the reaction product;
   v) evaporating, cooling, and filtering the solution of step (iv) to obtain a solid-phase product;
   vi) washing the solid-phase product of step (v) with water; and
   vii) drying the washed solid-phase product of step (vi).

13. The method of claim 12, further comprising: separating acetone oxime from the liquid obtained from the cooling and filtration process, and reusing the separated acetone oxime as at least part of the acetone oxime raw material in Step (b1).

14. The method of claim 2, wherein the weight ratio between the titanium-silicate molecular sieve catalyst and acetone of step (a) is 1:5-20, and the molar ratio among acetone, ammonia and hydrogen peroxide is 1:1-3:0.5-2.

15. The method of claim 5, wherein the weight ratio between the modified titanium-silicate molecular sieve catalyst and acetone oxime of step (b1) is 5-30:100, the weight ratio between water and acetone oxime is 1-10:1, and the molar ratio between acetone oxime and hydrogen peroxide is 1:1-3.

16. The method of claim 15, wherein the weight ratio between the modified titanium-silicate molecular sieve catalyst and acetone oxime of step (b1) is 10-15:100, the weight ratio between water and acetone oxime is 2-4:1, and the molar ratio between acetone oxime and hydrogen peroxide is 1:2-2.5.

17. The method of claim 8, wherein the weight ratio between the modified titanium-silicate molecular sieve catalyst and acetone of step (b2) is 5-30:100, the weight ratio between water and acetone is 1-5:1, and the molar ratio between acetone and hydrogen peroxide is 1:3-8.

18. The method of claim 17, wherein the weight ratio between the modified titanium-silicate molecular sieve catalyst and acetone of step (b2) is 10-15:100, the weight ratio between water and acetone is 2-4:1, and the molar ratio between acetone and hydrogen peroxide is 1:4-6.

19. The method of claim 11, wherein step (c) further comprises:
   i) cooling the reaction products of (b1) or (b2) to a temperature from about 0° C. to about 40° C.;
   ii) separating a solid phase of the reaction product from a liquid phase of the reaction product;
   iii) washing the solid phase of the reaction product with acetone;
   iv) mixing the solution of step (iii) with the liquid phase of the reaction product;
   v) evaporating, cooling, and filtering the solution of step (iv) to obtain a solid-phase product;
   vi) washing the solid-phase product of step (v) with water; and
   vii) drying the washed solid-phase product of step (vi).

20. The method of claim 19, further comprising: separating acetone oxime from the liquid obtained from the cooling and filtration process, and reusing the separated acetone oxime as at least part of the acetone oxime raw material in Step (b1).

* * * * *